(12) United States Patent
Vautrin

(10) Patent No.: US 10,034,754 B2
(45) Date of Patent: Jul. 31, 2018

(54) TAPER PROTECTION SYSTEM FOR ORTHOPEDIC IMPLANTS DURING POLISHING PHASES BY TRIBOFINISHING

(71) Applicant: Greatbatch Medical S.A., Clarence, NY (US)

(72) Inventor: Luc Vautrin, Mareilles (FR)

(73) Assignee: Greatbatch Medical S.A., Clarence, NY (US)

( * ) Notice: Subject to any disclaimer, the term of this patent is extended or adjusted under 35 U.S.C. 154(b) by 81 days.

(21) Appl. No.: 14/853,571

(22) Filed: Sep. 14, 2015

(65) Prior Publication Data

US 2016/0074167 A1    Mar. 17, 2016

Related U.S. Application Data

(60) Provisional application No. 62/049,609, filed on Sep. 12, 2014.

(51) Int. Cl.
*A61F 2/46* (2006.01)
*A61B 17/56* (2006.01)
(Continued)

(52) U.S. Cl.
CPC .......... *A61F 2/3609* (2013.01); *A61F 2/3094* (2013.01); *A61F 2/30721* (2013.01);
(Continued)

(58) Field of Classification Search
CPC .. A61F 2002/30672; A61F 2002/30738; A61F 2002/30772; A61F 2/468; A61B 2017/1205; A61B 17/1659; A61B 17/221
See application file for complete search history.

(56) References Cited

U.S. PATENT DOCUMENTS 6,093,209 A    7/2000 Sanders
2001/0001121 A1*    5/2001 Lombardo ........... A61B 17/154
606/89

(Continued)

OTHER PUBLICATIONS

"Orthopedic Implant and Medical Device Finishing", Rosier Metal Finishing USA, LLC, Publ.-Nr. US 253.00.

*Primary Examiner* — Ann Schillinger
(74) *Attorney, Agent, or Firm* — Steven W. Winn; Michael F. Scalise

(57) ABSTRACT

A surface protection system comprising a protective sleeve positionable over an orthopedic tool or implant, for example the tapered end of an orthopedioc femoral stem implant to shield the covered surface from exposure to abrasive particles during an automated polishing process is described. The protective sleeve comprises a body having an annular sidewall that extends from a proximal end to a distal end and is composed of a polymeric material. A cavity resides within the body extending through the distal end to a proximal end sidewall positioned perpendicular to the annular sidewall. The protective sleeve further comprises at least one annular recess intermediate at least two annular ridges that reside along an interior surface at the distal end of the sleeve. These series of annular ridges and recesses form a removably tight seal around the exterior surface that minimizes the migration of abrasive polishing particles to the exterior surface of the orthopedic tool or implant. The system further comprises an impactor and extractor tools which facilitate the positioning and removal of the protective sleeve from the surface thereof.

8 Claims, 11 Drawing Sheets

(51) Int. Cl.
  *A61F 2/36* (2006.01)
  *A61F 2/30* (2006.01)
(52) U.S. Cl.
  CPC ...... *A61F 2/46* (2013.01); *A61F 2002/30718* (2013.01); *A61F 2002/3625* (2013.01); *A61F 2220/0033* (2013.01)

(56) References Cited

U.S. PATENT DOCUMENTS

| | | |
|---|---|---|
| 2003/0144740 A1 | 7/2003 | Kolb et al. |
| 2004/0015238 A1 | 1/2004 | Buehler et al. |
| 2004/0254646 A1 | 12/2004 | Stone et al. |
| 2005/0015094 A1* | 1/2005 | Keller .................. A61F 2/4425 606/99 |
| 2008/0082175 A1 | 4/2008 | Holovacs et al. |
| 2009/0043397 A1 | 2/2009 | Park et al. |
| 2009/0112219 A1* | 4/2009 | Daniels ................. A61F 2/4607 606/99 |
| 2010/0241239 A1* | 9/2010 | Smith ................ A61B 17/1668 623/22.42 |
| 2012/0259423 A1 | 10/2012 | Carr et al. |
| 2013/0060346 A1 | 3/2013 | Collins et al. |

\* cited by examiner

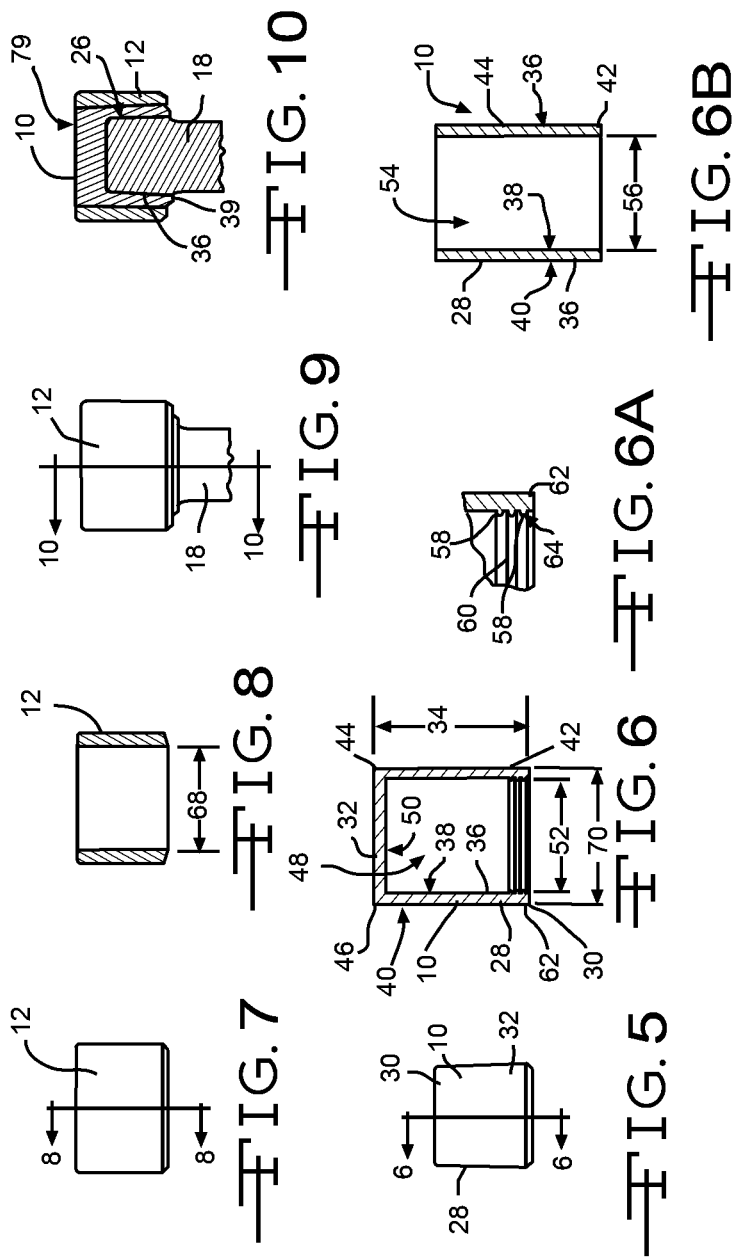

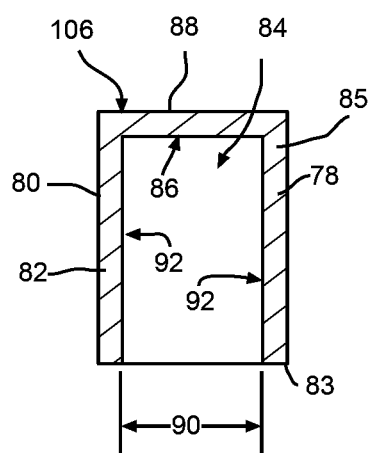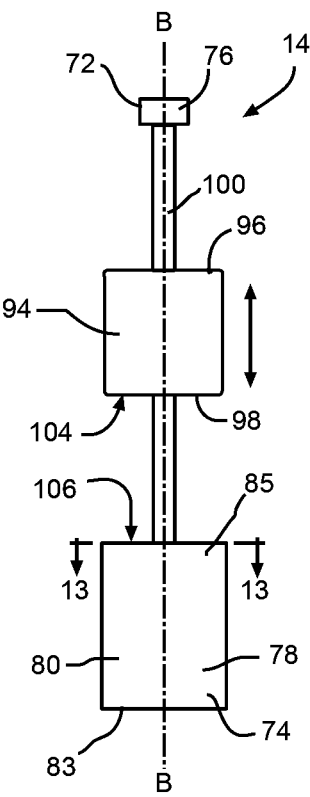

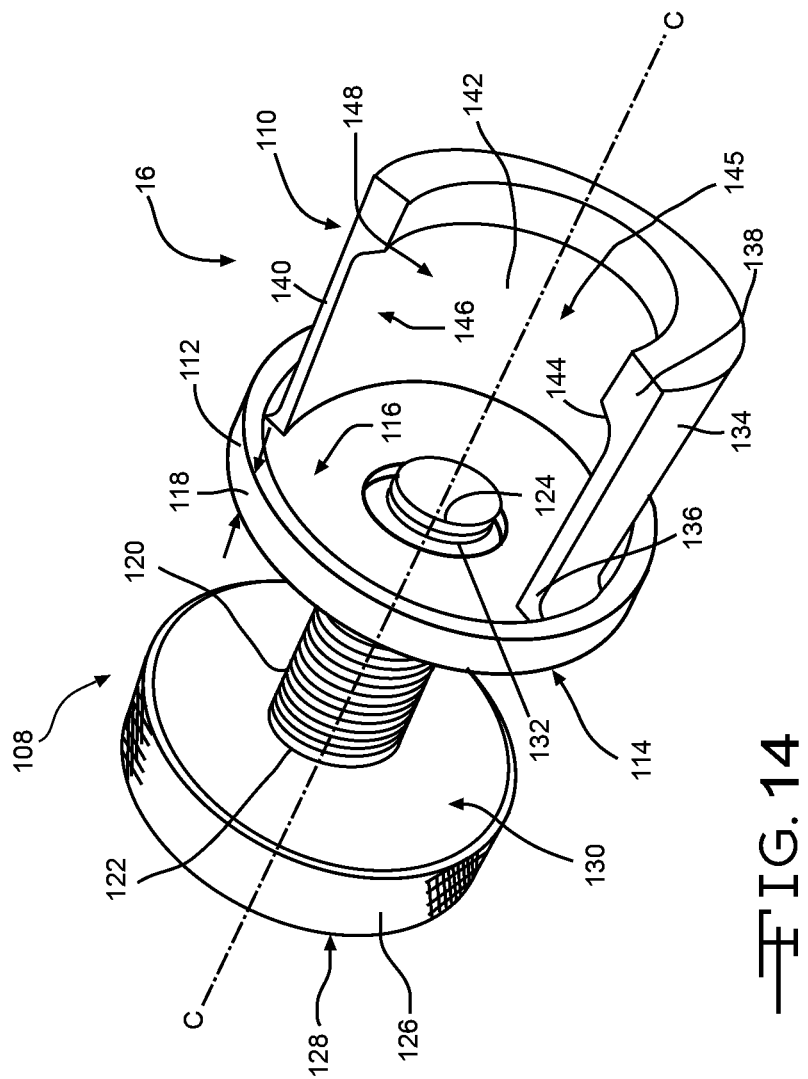

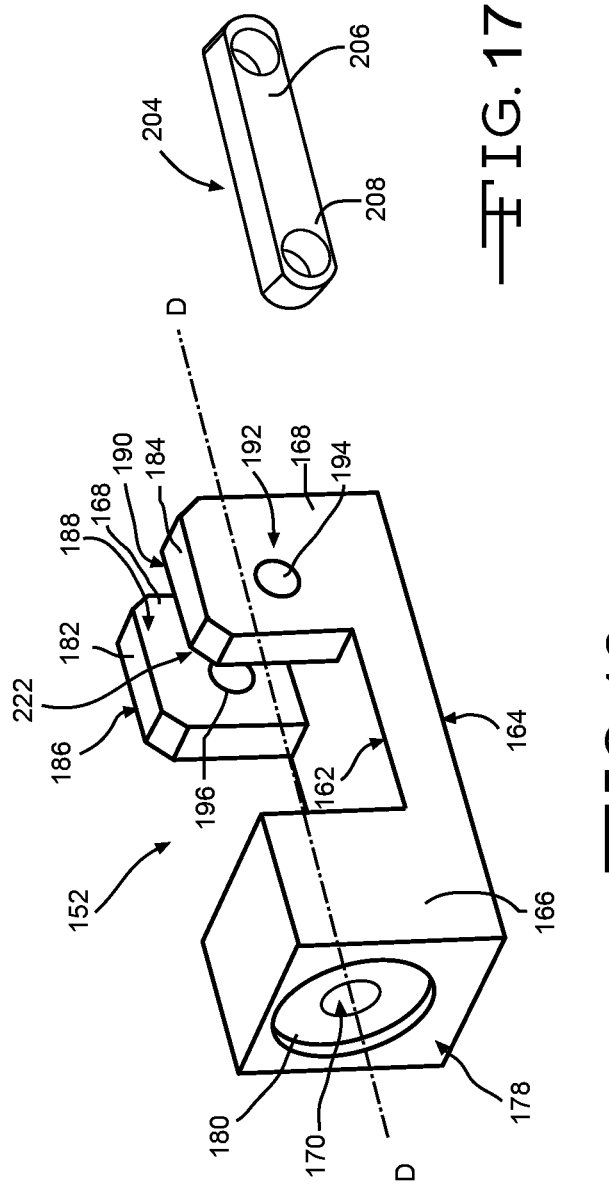

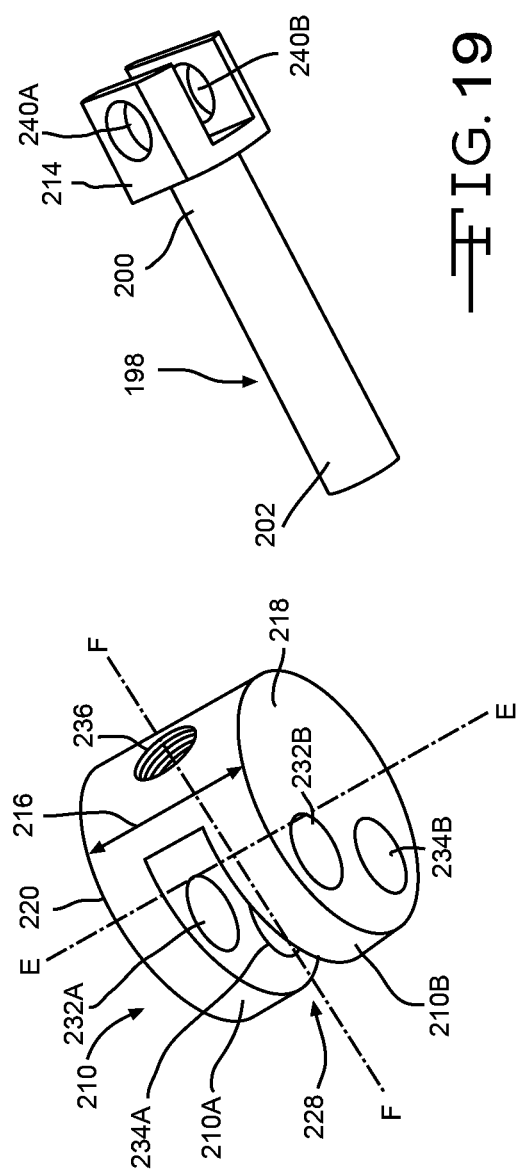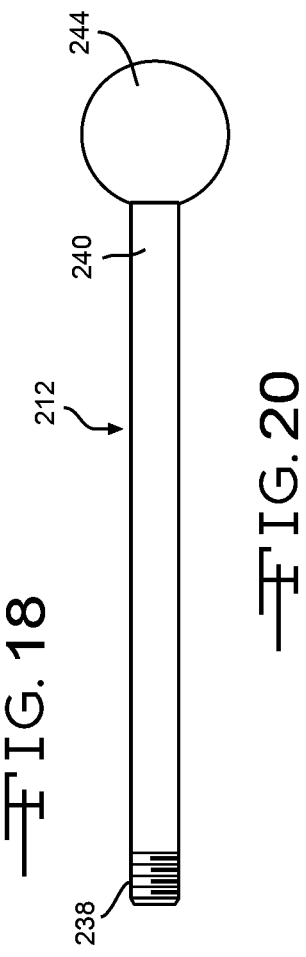

TAPER PROTECTION SYSTEM FOR ORTHOPEDIC IMPLANTS DURING POLISHING PHASES BY TRIBOFINISHING

CROSS REFERENCE TO RELATED APPLICATION

This application claims priority from U.S. Provisional Application Ser. No. 62/049,609, filed Sep. 12, 2015.

TECHNICAL FIELD

This invention relates to the art of instruments used in the manufacturing process of orthopedic tools and implants. More specifically, this invention relates to tooling used during the manufacture of orthopedic implants and instruments.

BACKGROUND OF THE INVENTION

A hip arthroplasty procedure is a surgical procedure in which the hip joint is replaced by a prosthetic implant. One such procedure is a total hip replacement procedure in which damaged bone and cartilage is removed and replaced with prosthetic components. During the procedure, the femoral head of the femur bone is removed and replaced with a femoral stem implant (FIGS. 3 and 4). Such implants are generally made of a biocompatible metallic material such as stainless steel. The metal stem portion is generally positioned within a hollow center of the femur. The stem may be press fit or cemented within the bone. A metal or ceramic ball, referred to as a prosthetic femoral head is placed on an upper tapered portion, i.e., a proximal tapered end of the stem implant. The prosthetic femoral head is received within a prosthetic cup that is implanted within the acetabulum.

Hip prostheses are typically manufactured to exacting dimensions and dimensional tolerances to ensure a proper fit that enables unobstructed movement of the body. In addition, these implants are generally manufactured with a smooth polished surface finish. This smooth polished finish helps minimize possible interference of the implant surface with surrounding tissue and bone. It is particularly desirable to remove surface imperfections such as burs from the surface of the implant. Such surface imperfections may rub against bone and tissue within the body, thereby potentially impeding patient mobility in addition to causing patient discomfort. Furthermore, such friction caused by the rubbing of implant surface imperfections with tissue and bone may negatively impact the longevity of the implant prosthetic components as such may lead to excessive mechanical wear that may result in undesirable repair or removal of the prosthetic implant.

As such, the exterior surfaces of these prosthetic implants, which are generally composed of a metallic material, are typically polished during the manufacturing process thereof. Polishing the surface of orthopedic implants generally minimizes surface imperfections and roughness, thereby minimizing potential interference of the implant surface with surrounding bone and tissue.

There are a number of different methods in which the surface of an orthopedic implant may be polished. One such polishing method is by manually polishing the implant. Such manual polishing processes are generally advantageous for polishing orthopedic implants having complex geometries as the manual polishing process can typically reach hidden surfaces within regions of the implant. In addition, the surface finish of the implant can be customized in that certain areas of the implant may comprise a varying surface roughness. However, such manual polishing methods are generally time consuming and, thus, are not desirable for an efficient manufacturing process.

Alternatively, an automatic polishing process can be used in which the orthopedic implants are polished by machine. One such automatic polishing technique is referred to as a "tribo-finishing" process. In the tribo-finishing process, a metal object, such as an orthopedic implant is immersed within a mixture that comprises abrasive polishing media. During the process multiple orthopedic implants are secured within a fixture that is immersed for a period of time within the mixture of abrasive polishing particles until a desirable surface finish is achieved. These orthopedic implants may be immersed multiple times in various abrasive polishing mixtures having different material compositions with different particle sizes and size distributions to achieve a desired surface roughness.

Since the object is immersed within a mixture of polishing media, tribo-finishing provides an efficient means in which the entire immersed surface is efficiently and evenly polished to a desired surface roughness. In addition, multiple objects can be polished automatically to a consistent surface finish at the same time. However, since the object is immersed within the polishing slurry media, it is difficult to selectively control the surface finish at different locations or regions along the surface of the object. For example, it may be desired to have a rougher surface finish along a handle portion to ensure an improved grip or attachment therebetween, but a smooth surface finish on another portion of the object.

Therefore, it is desired to utilize the efficient tribo-finishing processing while being able to selectively polish various surface areas to different surface finishes. Thus, the present invention provides a system which enables portions of a surface of an object, such as an orthopedic implant surface, to be selectively polished to a different surface roughness. More specifically, the present invention provides a protective sleeve and associated tooling that prevents an area of the surface from being exposed to the polish slurry mixture.

SUMMARY OF THE INVENTION

The present invention provides a system comprised of a protective sleeve and associated impaction and extraction tools that is designed to isolate at least a portion of an external surface of an orthopedic tool or implant from contact with the external environment. More specifically, the protective sleeve of the system is temporarily positioned on the end of an orthopedic tool or implant such that exposure of an external surface thereof to abrasive particles, such as those used in a tribo-finishing process, is minimized. Therefore, those surfaces that are isolated by the protective sleeve are not exposed to abrasive polishing particles, thus resulting in the selected surface remaining unpolished thereby having a more roughened surface finish in comparison to other polished surfaces areas.

It is generally desired that the external surface of orthopedic implants have a smooth polished surface, however, it may be desired for certain surface areas of the implant to have a more roughened surface finish. This roughened surface may help the attachment of a component to the implant or alternatively may help the adherence of the implant within the body. For example, an orthopedic femoral stem implant generally comprises an upper tapered portion on which a femoral ball is permanently affixed. Thus, it is generally desired for the tapered portion of the femoral stem implant to comprise a roughened surface to ensure a strong bond to the formal ball attachment.

In an embodiment, the surface protection system comprises a protective sleeve which is positioned over an area of a surface, such as the upper tapered portion of a femoral stem implant, such that exposure to abrasive polishing particles is minimized. In addition, the system comprises an impactor tool that positions the protective sleeve on the implant or object. Furthermore, the system comprises an extractor tool that is designed to remove the protective sleeve from the implant.

In a preferred embodiment, the protective sleeve comprises a body having a cavity that at least partially extends therewithin. Alternatively, the protective sleeve may comprise a through-bore that extends lengthwise through the thickness of the sleeve. The protective sleeve is preferably composed of a polymer material that ensures a compliant interference fit with the external surface of the implant or tool. In addition, the system comprises an impactor tool that exerts an axial mechanical force on the protective sleeve thus positioning the sleeve over a desired portion of a tool or implant. A ring may be positioned about the exterior of the protective sleeve. The ring provides additional rigidity and mechanical strength to the sleeve and, in addition, helps position the protective sleeve over the desired surface area by focusing the force exerted by the impactor on the sleeve. For example, the ring facilitates the transfer of the mechanical force exerted by the impactor to the protective sleeve. Furthermore, the system comprises an extractor tool that is designed to remove the protective sleeve from the tool or implant.

BRIEF DESCRIPTION OF THE DRAWINGS

FIG. 5 is a side view of an embodiment of the protective sleeve of the present invention.

FIG. 6 is a cross-sectional view of the protective sleeve illustrated in FIG. 5.

FIG. 6A illustrates a magnified cross-sectional view of the protective sleeve illustrated in FIG. 5 taken at the protective sleeve distal end.

FIG. 6B is a cross-sectional view of an alternative embodiment of a protective sleeve comprising a throughbore that extends along longitudinal axis A-A.

FIG. 7 is a side view of an embodiment of the ring that may be positioned around the protective sleeve.

FIG. 8 is a cross-sectional view of the ring illustrated in FIG. 7.

FIG. 9 is a side view of an embodiment of the protective sleeve and ring subassembly of FIG. 1 positioned at the end of an orthopedic tool.

FIG. 10 is a cross-sectional view of the embodiment of the protective sleeve and ring subassembly shown in FIG. 9.

FIG. 12 is a side view of the protective sleeve impactor tool shown in FIG. 11.

FIG. 13 is a cross-sectional view of the coupling portion of the impactor shown in FIG. 11.

FIG. 14 is an embodiment of a protective sleeve extractor tool used to remove the sleeve from the end of an orthopedic femoral stem implant.

FIG. 16 is a perspective view of an embodiment of a platform portion of the extractor tool illustrated in FIG. 15.

FIG. 17 shows an embodiment of an intermediate rod that comprises the extractor tool illustrated in FIG. 15.

FIGS. 18, 18A, and 18B illustrate an embodiment of a cam comprised within the extractor tool illustrated in FIG. 15.

FIG. 19 shows an embodiment of a drive rod comprised within the extractor tool illustrated in FIG. 15.

FIG. 20 illustrates an embodiment of an action lever of the extractor tool illustrated in FIG. 15.

DETAILED DESCRIPTION OF THE PREFERRED EMBODIMENT

Figure 1:
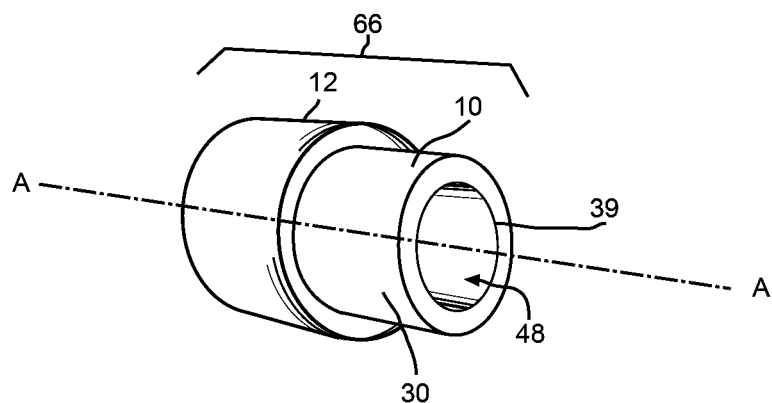
FIG. 1 illustrates an embodiment of a protective sleeve and ring subassembly that comprises the surface protection system of the present invention.
Figure 2:
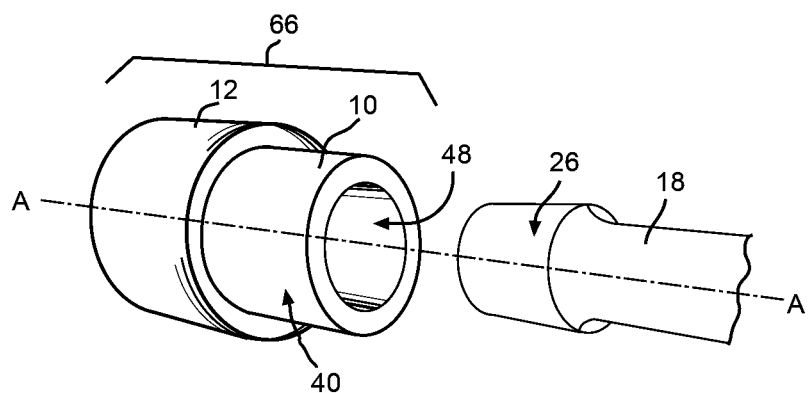
FIG. 2 illustrates an embodiment of the protective sleeve and ring subassembly shown in FIG. 1 being positioned at the end of an orthopedic tool.

Now turning to the figures, FIGS. 1-6, 6A, 6B, 7-18, 18A, 18B, 19, and 20 illustrate preferred embodiments of a surface protection system of the present invention. As illustrated, the system comprises a protective sleeve 10 (FIGS. 1-6, 6A and 6B), an annular ring 12 (FIGS. 1-4 and 7-10) positionable about an exterior surface of the protective sleeve 10, a protective sleeve impactor 14 (FIG. 11-13) and a protective sleeve extractor 16 (FIG. 14). The protective sleeve 10 is designed to temporarily cover at least a portion of an exterior surface of an object, such as an orthopedic implant or tool 18, from the external environment (FIG. 2). More preferably, the protective sleeve 10 of the system of the present invention is intended to be removably positioned over a portion of an orthopedic implant or tool 18 to isolate at least a portion of an exterior surface thereof from exposure to abrasive polishing materials. The impactor and extractor tools 14, 16 facilitate the positioning and removal, respectively, of the protective sleeve 10 from the object, i.e., an orthopedic tool or implant 18. The annular ring 12 is designed to be positioned about the exterior of the protective sleeve 10. The ring 12 serves to provide added mechanical structure and rigidity to the protective sleeve 10 particularly during positioning and removal of the sleeve 10.

Figure 3:
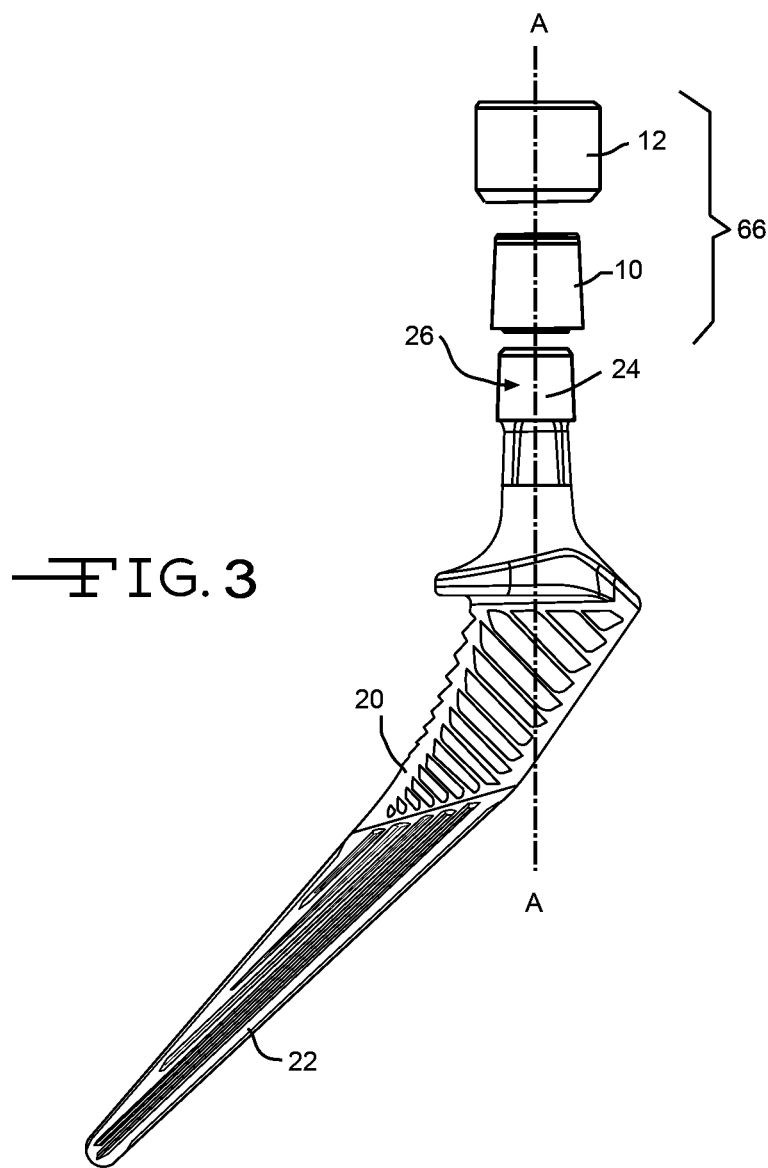
FIGS. 3 and 4 show an embodiment of the protective sleeve and ring subassembly of FIG. 1 positioned over a tapered end of an orthopedic femoral stem implant.
Figure 4:
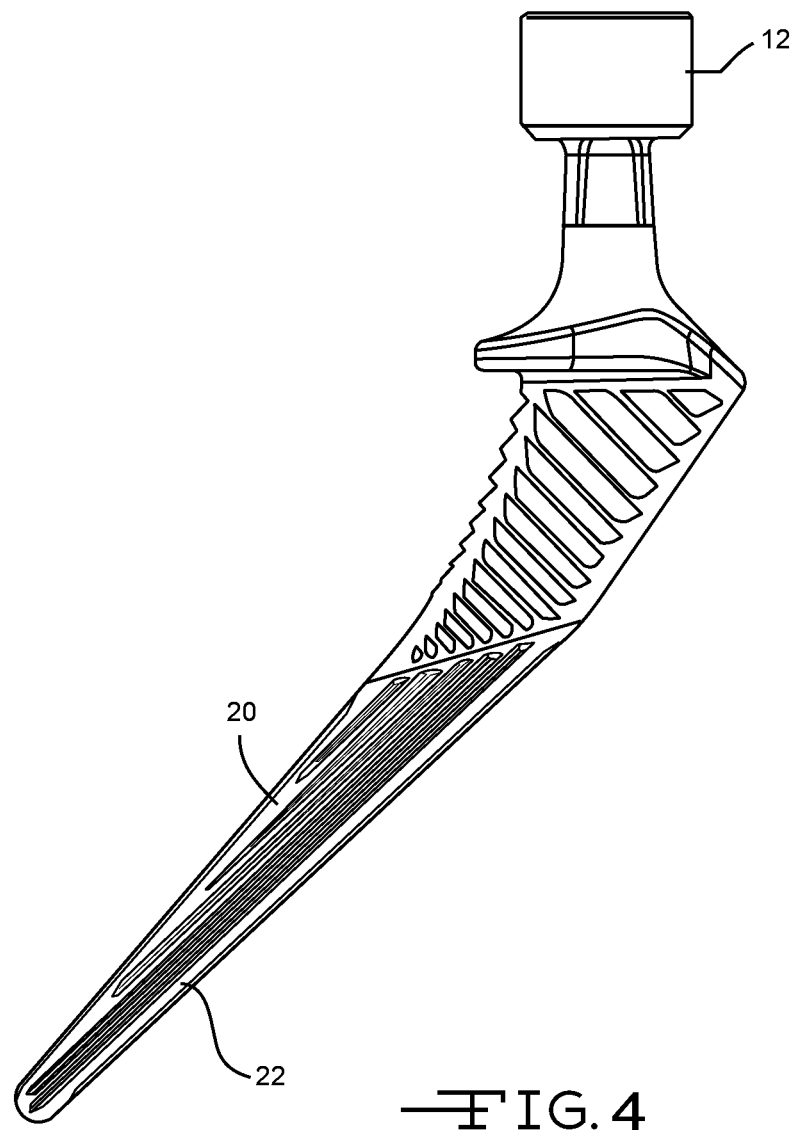

In a preferred embodiment, the protective sleeve 10 is removably positioned over at least a portion of an orthopedic femoral stem implant 20 as illustrated in FIGS. 3 and 4. Femoral stem implants are generally used in orthopedic hip replacement procedures. The implant is inserted into the body to support the femur bone with the acetabulum of a patient. As shown, the femoral stem implant 20 comprises a distal stem portion 22 spaced from a proximal tapered end 24 having a tapered end surface 26 that extends circumferentially around the tapered end 24 and downwardly and outwardly toward stem implant 20. The distal stem portion 22 is implanted within the femur bone. The proximal tapered end 24 supports a prosthetic femoral head (not shown) that is positioned within the acetabulum. It is important that the connection between the prosthetic femoral head and the proximal tapered end 24 of the implant 20 is of a strong permanent bond. This ensures that the femoral head does not move or become detached from the femoral stem implant as the patient moves. As such, it is important that the surface 26 of the proximal tapered end 24 of the femoral stem implant 20 has a roughened finish. This helps to ensure that the prosthetic femoral head permanently bonds to the tapered end 24. Thus, by removably positioning the protective sleeve 10 over the tapered end 24 of the orthopedic stem implant 20, the covered surface therewithin is isolated from exposure to the abrasive particles that comprise the polishing process, particularly the abrasive media of the tribo-polishing process. The external surface 26 of the tapered proximal end 24 is not exposed to the abrasive polishing media, and the surface thereof, remains unpolished and roughened in comparison to other surface areas of the implant 20 that are polished. As defined herein, "tribo-finishing" is a method of polishing an external surface, such as a metallic surface, using a mixture of abrasive particles. During the "tribo-finishing" process, an object that is desired to be polished is immersed within the mixture of abrasive particles. Thus, the surface that is immersed and exposed to the abrasive particle mixture is rendered to have a smooth polished surface finish.

Furthermore, in a preferred embodiment the protective sleeve 10 forms a tight interference fit with the covered exterior surface of the implant 20 or tool 18. This helps prevent the covered exterior surface of the implant from being exposed to the environment. More specifically, the tight interference fit created by the protective sleeve 10 significantly minimizes the possibility that the surface under the protective sleeve may become exposed to the polishing materials, particularly the abrasive particle mixture used in the tribo-finishing process.

The protective sleeve 10 of the present invention is preferably made of a polymeric material. The polymeric material is designed to provide a pliable and conformal fit about an external surface of the orthopedic tool 18 or implant 20. The conformal fit provided by the pliable polymeric material helps to prevent the covered surface from becoming exposed to the abrasive polishing particles. In a preferred embodiment, the polymeric materials may include, but are not limited to neoprene, silicone, ethylene propylene diene monomer (EPDM), fluorosilicone, natural rubber, nitrile, a fluoroelastomer and combinations thereof.

As shown in FIGS. 1, 2, 3, 5, 6, 6A, 6B, and 10 the protective sleeve 10 comprises a protective sleeve body 28 having a distal end 30 spaced from a proximal end 32. A longitudinal axis A-A extends along an elongated length 34 of the body 28 of the sleeve 10. An annular elongated body sidewall 36, having an interior sidewall surface 38 and an opposing exterior sidewall surface 40, extends between the distal and proximal ends 30, 32 to form the body 28 of the sleeve 10.

In a preferred embodiment, the annular sidewall 36 extends downwardly and outwardly along axis A-A from the proximal end wall 32 to a distal edge 39. This structure gives sleeve 10 a frusto-conical shape and helps enable an interference fit therewith. As illustrated in FIGS. 6 and 6B, a distal end sidewall 42 of the annular body sidewall 36 meets a proximal end sidewall 44 at the proximal end 32 of the sleeve body 28. In a preferred embodiment, the outer diameter at the distal end sidewall 42 is greater than the outer diameter at the proximal end wall 32. The proximal end 32 of the sleeve 10 may comprise a beveled surface 46 having a radius of curvature ranging from about 0.13 cm (0.05 inches) to about 0.50 cm (0.20 inches).

As shown in FIGS. 1, 2, 6, and 10, a cavity 48 resides within the body 28 of the protective sleeve 10. More specifically, the cavity 48 extends through the proximal end 30 of the sleeve 10 to an interior surface 50 of the distal end sidewall 44. The cavity 48 defines an inner protective sleeve diameter 52 that spans across diametrically opposed interior surfaces of the annular body sidewall 36. In a preferred embodiment, the inner diameter 52 of the protective sleeve 10 ranges from about 1 cm to about 7 cm. The inner diameter 52 of the body 28 of the sleeve 10 is designed to provide an interference fit over at least a portion of an orthopedic implant or tool 18. For example, the inner diameter 52 provides an interference fit over the proximal tapered portion 24 of an orthopedic femoral stem implant 20. In that respect, the frusto-conical taper of the inner surface of sleeve 10 substantially matches the taper of portion 24 of the implant.

In an alternative embodiment illustrated in FIG. 6B, the protective sleeve 10 may comprise a throughbore 54 that extends along longitudinal axis A-A through the thickness of the protective sleeve body 28. The annular sidewall 36 defines the throughbore 54 of the protective sleeve 10 illustrated in FIG. 6B. In a preferred embodiment, the throughbore 54 may comprise a throughbore diameter 56 that ranges from about 0.5 cm to about 3 cm.

As shown in FIGS. 6 and 6A, the protective sleeve 10 may comprise at least one interior rib 58 and at least one interior recess 60. The rib 58 and recess 60 reside at a base portion 62 located at the distal end 30 of the protective sleeve 10. More specifically, the rib 58 and recess 60 are positioned along an annular interior surface 64 of the base portion 62 of the sleeve 10. The protective sleeve 10 may be constructed such that the rib 58 and recess 60 are positioned along the interior surface 64 of the base portion 62 in an alternating fashion such that there is at least one annular recess 60 intermediate two annular ribs 58. This configuration helps ensure a tight interference fit of the protective sleeve 10 on a portion of an orthopedic tool 18 implant 20. The ribs 58 and at least one recess 60 are preferably positioned in a perpendicular orientation to longitudinal axis A-A such that they continuously circumnavigate the longitudinal axis. In addition, it is preferred that each of the ribs 58 protrudes from the interior surface 64 of the base portion 62 and extends into the cavity 48. The recess 60 is further recessed, at least partially, into the interior surface 64 of the base portion 62. In a preferred embodiment, each of the rib portions 58 protrudes from the interior surface 64 into the cavity 48 by about 0.1 cm to about 0.5 cm. Furthermore, it is preferred that each of the ribs 58 comprise a curved exterior surface. The combination of the annular ribs 58 and at least one recess 60 create a gripping surface, which forms an interference fit particularly when positioned over the tapered portion 24 of a femoral stem implant 20.

As shown in FIGS. 1, 2, 3, 4, 7, 8, 9 and 10, the annular ring 12 may be positioned around the outer perimeter of the protective sleeve 10, thus forming a subassembly 66 comprised of the protective sleeve 10 and annular ring 12. The annular ring 12 may be constructed having an inner diameter 68 that is less than an outer diameter 70 of the distal end 32 of the protective sleeve 10. In this way, the annular ring 12 forms an interference fit with that of the outer sidewall surface 40 of the protective cover 10. In addition, the annular ring 12 may also comprise a frusto-conical shape having an outer diameter at the distal end that is greater than an outer diameter at the proximal end. In a preferred embodiment, the inner diameter 68 of the annular ring 12 may range from about 0.5 cm to about 3 cm. The annular ring 12 is also preferably composed of a metallic material. Examples of which may include, but are not limited to, stainless steel, nickel, copper, and alloys thereof. As will be described in more detail hereinafter, the annular ring 12 provides added rigidity to the protective sleeve 10 such that the force exerted by the impactor 14 drives the protective sleeve 10 in an axial direction along the tapered portion 24 of the implant 20. In a preferred embodiment, the taper portion 24 mates with the inner taper of the frusto-conical sleeve 10. More preferably, the shape of the taper portion 24 matches the inner taper of the frusto-conical sleeve 10. Once the protective sleeve 10 is positioned at a desired location, the annular ring 12 may be removed.

Figure 11:
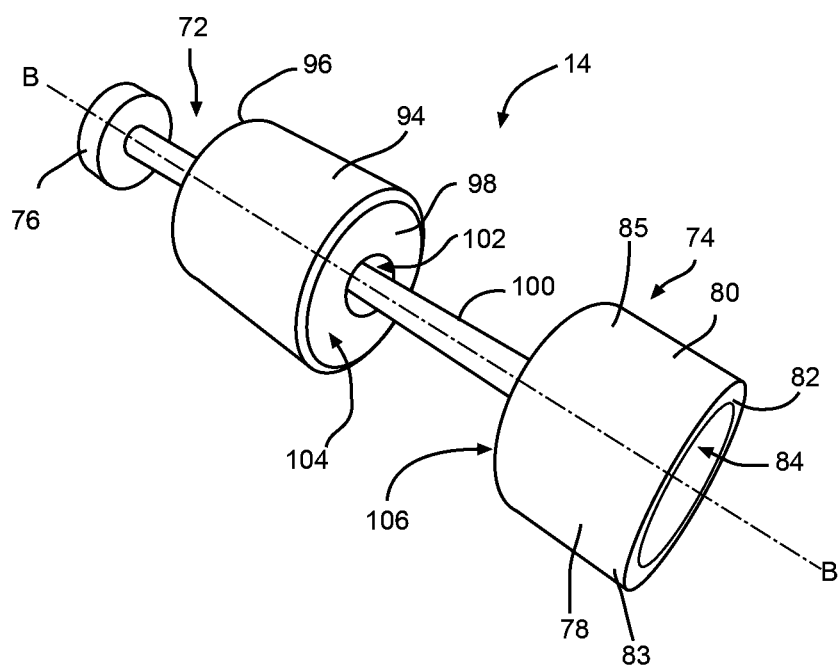
FIG. 11 illustrates an embodiment of a protective sleeve impactor tool used to position the sleeve on the end of an orthopedic femoral stem implant.

FIGS. 11, 12 and 13 illustrate an embodiment of the impactor 14 that may be used to position the protective sleeve 10 or sleeve 10/ring 12 subassembly 66 thereof on a tapered portion 24 of a femoral stem implant 20. As shown, the impactor 14 comprises an impactor proximal end 72 spaced from an impactor distal end 74. A longitudinal axis B-B extends lengthwise along a rod 100 and through the respective impactor proximal and distal ends 72, 74. As illustrated in FIG. 11, the impactor 14 comprises an impactor plate 76 that resides at the proximal end 72 of the rod 100 and a coupling portion 78 that resides at the distal end 74 of the rod 100. The impactor plate is oriented such that its thickness extends about perpendicular to longitudinal axis B-B. The coupling portion 78 comprises a coupling body 80 having a coupling body distal end 83 spaced from a coupling body proximal end 85. An annular coupling sidewall 82 defines a coupling cavity 84 that at least partially extends within the coupling body 80 at the distal end 83.

As illustrated in FIG. 13, the cavity 84 extends through the distal end 83 of the coupling body 80 to an interior surface 86 of a proximal end cavity sidewall 88. The cavity 84 defines an inner coupling diameter 90 that spans across diametrically opposed interior surfaces 92 of the coupling portion 78. In a preferred embodiment, the coupling portion 78 is configured to be positioned over the protective sleeve 10 or sleeve 10/ring 12 subassembly 66 thereof. More specifically, the protective sleeve 10 or subassembly 66 thereof is positioned within the coupling cavity 84 such that a proximal end surface 79 of the protective sleeve 10 is in contact with the interior surface 86 of the cavity 84. In a preferred embodiment, the inner diameter 90 of the coupling body 80 ranges from about 0.5 cm to about 5 cm.

A hammer weight 94 having opposed proximal and distal hammer ends 96, 98 resides between the impacting plate 76 and the coupling portion 78 along a rod 100 that extends therebetween along longitudinal axis B-B. As illustrated in FIG. 11, the hammer weight 94 comprises a throughbore 102 that extends lengthwise through the thickness of the weight 94. In a preferred embodiment, the rod 100 extends through the throughbore 102 of the weight 94. In a preferred embodiment, the weight 94 is capable of axial movement along the rod 100 and longitudinal axis B-B. Once the cavity 84 of the coupling portion 78 of the impactor 14 is positioned over the protective sleeve 10 or sleeve 10/ring 12 subassembly 66, the hammer weight 94 is moved axially along rod 100 to impart a force to the sleeve 10 or subassembly 66 that positions either to a desired location along the tool 18 or implant 20.

As previously discussed, the distal end 30 of the protective sleeve 10 is preferably positioned over the proximal tapered portion 24 of a femoral stem implant 20. The annular ring 12 may be positioned about the exterior surface 40 of the protective sleeve 10 at the distal end 30, thus creating the protective sleeve 10/annular ring 12 subassembly 66. Alternatively, the protective sleeve 10 may be positioned over the tapered portion 24 of the femoral stem implant 20 without the annular ring 12. The protective sleeve 10 or sleeve 10/ring 12 subassembly 66 is positioned within the cavity 84 of the coupling portion 78 of the impactor 14. In a preferred embodiment, the hammer weight 94 is moved in a back and forth axial direction along rod 100 such that it forcibly contacts an exterior surface 106 at the proximal end 85 of the coupling portion 78, thereby imparting a force from the hammer weight 94 to the coupling portion 78. More specifically, a distal surface 104 residing at the distal end 98 of the weight 94, contacts the exterior surface 106 at the proximal end of the coupling 78. The force exerted by the hammer 94 to the coupling portion 78 is in turn imparted to the protective sleeve 10 or subassembly 66 thereof. This impaction force drives either of the protective sleeve 10 or sleeve 10/ring 12 subassembly 66 further in a distal direction along the tapered portion 24 of the implant 20, thereby wedging either in place on the tapered portion 24 of the implant 20.

FIG. 14 illustrates an embodiment of the extractor tool 16 that may be used to remove the protective sleeve 10 or sleeve 10/ring 12 subassembly 66. As illustrated, the extractor 16 comprises an extractor proximal end 108 spaced from an extractor distal end 110. More specifically, the extractor 16 comprises an extractor plate 112 having opposing top and bottom plate surfaces 114, 116 and a plate thickness 118 therebetween. An imaginary longitudinal axis C-C extends about perpendicularly through the thickness 118 of the plate 112. A threaded member 120 having opposing proximal and distal threaded member ends 122, 124 is connected to an extractor handle 126 having opposed proximal and distal handle surfaces 128, 130. As illustrated in FIG. 14 the threaded member proximal end 122 extends outwardly from the extractor handle distal surface 130. The distal threaded member end 124 is received within a threaded opening 132 that extends through the extractor plate thickness 118. In a preferred embodiment, the opening 132 is oriented about perpendicular with respect to longitudinal axis C-C. A socket 134 having a socket proximal end 136 spaced from a socket distal end 138 extends from the bottom surface 116 of the extractor plate 112.

As illustrated in FIG. 14, the socket 134 comprises a socket sidewall 140 that extends about perpendicular from the extractor plate bottom surface 116. In a preferred embodiment, the sidewall 140 at least partially extends in an annular orientation about the perimeter of the extractor plate 112. The sidewall 140 defines a socket interior 142 within which the protective sleeve 10 or subassembly 66 thereof may be positioned. A rim 144 resides at the distal end 138 of the socket 134 and defines a distal socket opening 145. In a preferred embodiment, the rim 144 resides at the socket distal end 134 along the curvature of the interior socket surface 146. The rim 144 at least partially circumnavigates longitudinal axis C-C and, in addition, extends inwardly towards longitudinal axis C-C from interior socket sidewall surface 146 at the distal end 138 thereby forming socket distal opening 145.

As shown, a portion of the socket sidewall 140 is removed, thus forming a side opening 148 through which the protective sleeve 10 or the protective sleeve sleeve 10/ring 12 subassembly 66 is positioned therewithin. In a preferred embodiment, the protective sleeve 10 or sleeve 10/ring 12 subassembly 66 may be slid through the side opening 148 of the socket sidewall 140 such that the inwardly extending rim 144 is in physical contact with the proximal end surface 79 of the protective sleeve 10 or sleeve 10/ring 12 subassembly 66. The rim 144 is designed to abut the proximal end 32 of the sleeve 10 to thereby capture the protective sleeve 10 or sleeve 10/ring 12 subassembly 66 within the socket 134 such that either is prevented from exiting the socket distal end 138.

In a preferred embodiment, once the protective sleeve 10 or sleeve 10/ring 12 subassembly 66 is positioned within the interior 148 of the socket 134, the handle 126 is rotated in either a clockwise or counterclockwise manner such that the distal end 124 of the threaded member 120 is positioned in contact with the proximal end surface 79 of the protective sleeve 10 or sleeve 10/ring 12 subassembly 66. In addition, the threaded member 120 is extended such that the distal end surface of the protective sleeve 10 or sleeve 10/ring 12 subassembly 66 is in contact with the rim 144 at the distal end 138 of the socket 134. Thus, the threaded member 120 and rim 144 secure opposing sides of the protective sleeve 10 or sleeve 10/ring 12 subassembly 66 within the interior 148 of the socket 134. Once the protective sleeve 10 or subassembly 66 thereof is secured therewithin, a force applied in a proximal direction, towards the extractor handle 126, is exerted on the sleeve 10 or subassembly 66 to thereby remove it from the end of the orthopedic tool 18 or implant 20. In a preferred embodiment, the force is applied at the interface between the rim surface and the distal surface of the sleeve 10 or sleeve 10/ring 12 subassembly 66. In a preferred embodiment, the tapered portion 24 of the implant 20 exits the distal socket opening 145 leaving the protective sleeve 10 or sleeve 10/ring 12 subassembly 66 thereof behind in the socket interior.

FIGS. 15, 16, 17, 18, 18A, 18B, 19, and 20 illustrate an alternate embodiment of a protective sleeve extractor 150 and components thereof that may be used with the surface protection system of the present invention. As shown, the extractor 150 comprises a platform 152 having a proximal platform end 154 that extends to a distal platform end 156 on which an extractor mechanism 158 is positioned.

Figure 15:
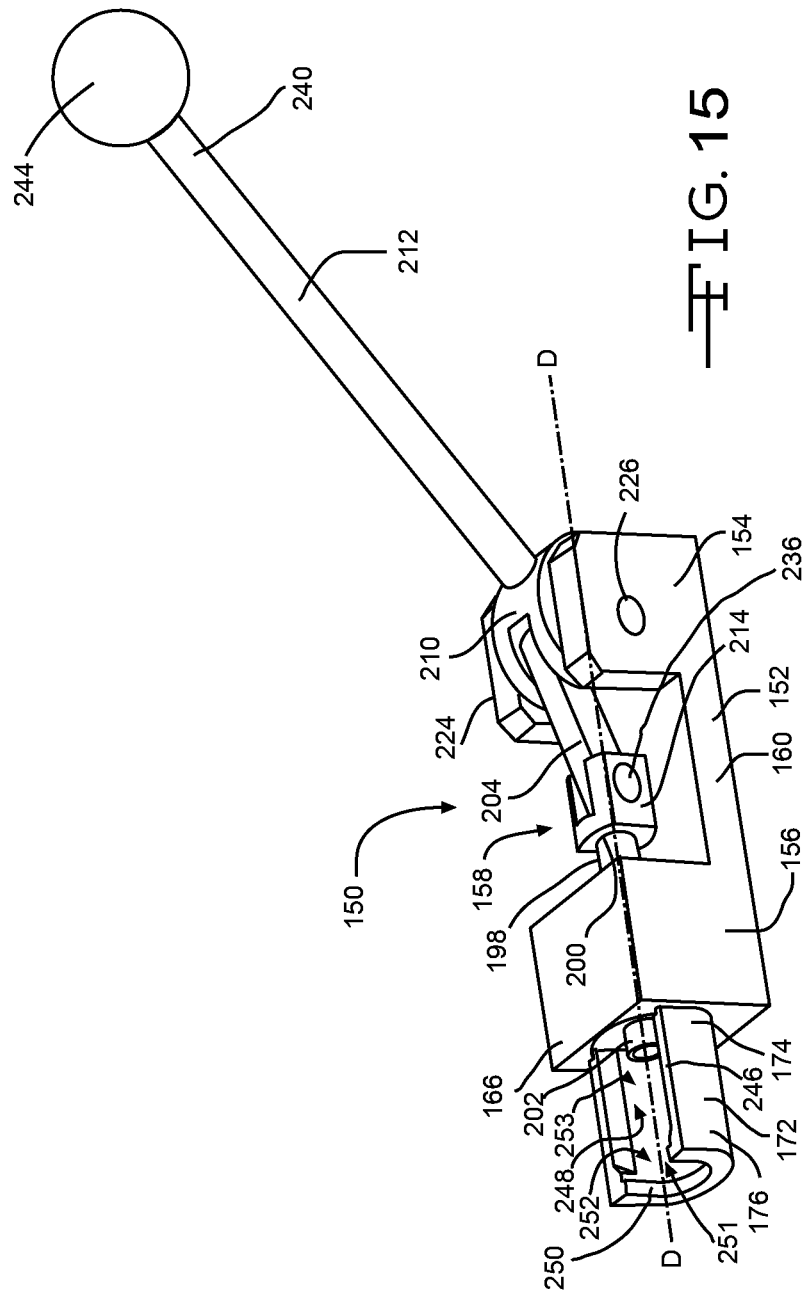
FIG. 15 illustrates an alternative embodiment of a protective sleeve extractor tool used to remove the sleeve from the end of an orthopedic femoral stem implant.

FIGS. 15 and 16 illustrate an embodiment of the platform 152. As shown, the platform 152 comprises an elongated base portion 160 having opposing top and bottom base portion surfaces 162, 164 that extend lengthwise along imaginary longitudinal axis D-D. In addition, spaced apart distal and proximal platform supports 166, 168 (FIG. 16) extend upwardly from the top base surface 162 at respective distal and proximal platform ends 156, 154. In a preferred embodiment, the distal and proximal supports 166, 168 extend perpendicularly from longitudinal axis D-D. The distal support 166 comprises a column structure having a distal support throughbore 170 that extends about perpendicular through the column support structure thickness along longitudinal axis D-D. A socket 172 having a socket proximal end 174 spaced from a socket distal end 176 extends longitudinally from a distal sidewall surface 178 of the distal support 166. As illustrated in FIG. 16, the proximal end 174 of the socket 172 may be received within a recess 180 that extends at least partially within the distal end sidewall surface 178 of the distal support 166.

The proximal support 168 extends upwardly from the top platform surface 162 at the opposite proximal end 154 of the platform 152. In a preferred embodiment, the proximal support 168 comprises spaced apart left and right sidewalls 182, 184 each sidewall comprising first and second major faces 186, 188, 190, 192. A gap 222 separates respective left and right sidewalls 182, 184. In a preferred embodiment, the left and right sidewalls 182, 184 are positioned facing each other. More specifically, the sidewalls 182, 184 are positioned such that the second major face 188 of the left sidewall 182 faces the first major face 190 of the right sidewall 184. In addition, as illustrated in FIG. 16, a first hole 194 extends through the thickness of the right sidewall 184. A second hole 196 extends through the thickness of the left sidewall 182. In a preferred embodiment the first and second holes 194, 196 are positioned directly across from each other.

As illustrated in FIG. 15, the socket 172 extends distally from the exterior surface 178 of the left platform support 166. As shown, the socket 172 comprises a socket proximal end 174 spaced from a socket distal end 176 that extends from the exterior surface 178 of the left platform support 166. As illustrated in FIG. 15, the socket 172 comprises a socket sidewall 246 that extends about perpendicular from the left support exterior surface 178. In a preferred embodiment, the socket sidewall 246 extends at least partially in an annular orientation about longitudinal axis D-D. The sidewall 246 defines a socket interior 248 within which the protective sleeve 10 or sleeve 10/ring 12 subassembly 66 may be positioned within. In addition, a rim 250 resides at the distal end 176 of the socket 172. In a preferred embodiment, the rim 250 extends inwardly towards longitudinal axis D-D that extends through the through-bore opening 170 of the left support 166. As illustrated in FIG. 15, rim 250 at least partially circumnavigates longitudinal axis D-D and, in addition, extends inwardly towards longitudinal axis D-D from interior socket sidewall surface 253 at the distal end 138 thereby defining a socket distal opening 251.

In a preferred embodiment, a portion of the sidewall 246 is removed, thus forming a side opening 252 through which the protective sleeve 10 or the sleeve 10/ring 12 subassembly 66 may be positioned therewithin. In a preferred embodiment, the protective sleeve 10 may be slid through the socket sidewall side opening 252 such that the inwardly extending rim 250 is positioned at the distal end of the protective sleeve or the sleeve 10/ring 12 subassembly 66. The rim 250 is designed to prevent the sleeve 10 or the sleeve 10/ring 12 subassembly 66 from exiting through the socket distal end 172.

FIGS. 16, 18, 19, 19A, 19B, 20, and 21 illustrate an embodiment of the extractor mechanism 158 and associated components thereof. As illustrated, the extractor mechanism 158 comprises a drive shaft 198 having spaced apart proximal and distal drive shaft ends 200, 202, a linkage 204 having spaced apart proximal and distal linkage ends 206, 208, a cam 210 and an actuation lever 212 having spaced apart proximal and distal lever ends 238, 240. In a preferred embodiment, the drive shaft 198 is received longitudinally through the distal support throughbore 170. As illustrated, the drive shaft proximal end 200 comprises a "U" joint 214 that connects to the linkage distal end 208. The linkage proximal end 206 is connected to the cam 210 and the proximal end 238 of the actuation lever 212 is also connected to the cam 210.

Figure 18B:
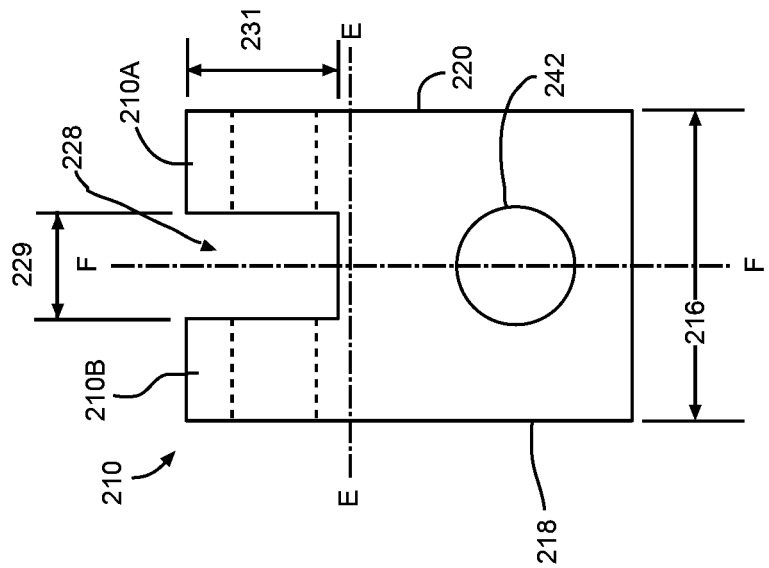
Figure 18A:
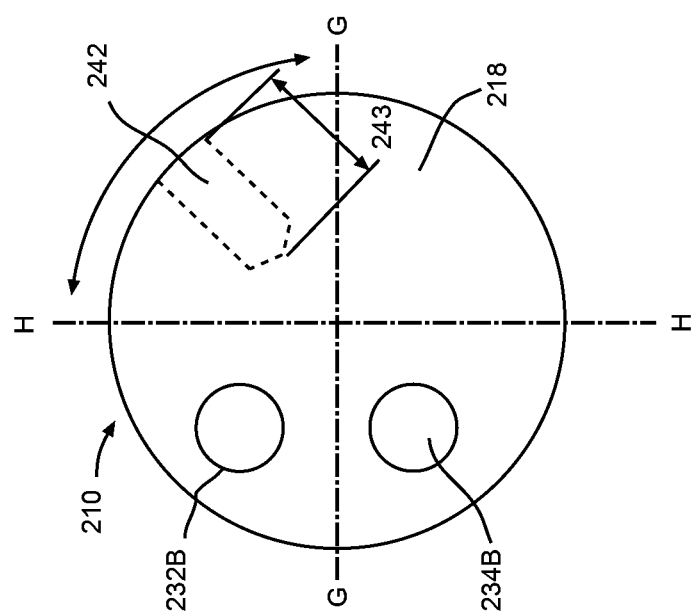

FIGS. 18, 18A, and 18B illustrate magnified views of the embodiment of the cam 210 illustrated in FIG. 15. As shown, the cam 210 comprises a cam thickness 216 that extends between first and second opposing cam sides 218, 220. As illustrated in FIG. 18, imaginary line E-E extends perpendicular to the cam thickness 216 and imaginary line F-F extends perpendicular to imaginary line E-E. As shown, imaginary line F-F provides a separation line between two cam halve portions, a left cam portion 210A and an opposing right cam portion 210B. In a preferred embodiment, the cam 210 is positioned within the gap 222 that extends between opposing first and second sidewalls 182, 184 that form the right platform support 168. In a preferred embodiment, the cam 210 is positioned within the gap 222 such that the opposing first and second sidewall cam sides 218, 220 are facing first and second major faces 190, 188 of the right and left platform sidewalls 184, 182, respectively. A first pin 224 is positioned along imaginary line E-E through opening 196 of the left sidewall 182 and opening 232A that at least partially through a portion of the thickness of the right cam portion 210A. A second pin 226 is positioned along imaginary line E-E through opening 194 of the right sidewall 184 and opening 232B that at least partially through a portion of the thickness of the left cam portion 210B thereby securing the cam 210 within the gap 222 between left and right sidewalls 182, 184. The cam 210 secured between respective left and right sidewalls 182, 184 such that it is capable of rotating in either a clockwise or counterclockwise direction with respect to imaginary axis E-E. More specifically, at least one of the first and second pins 224, 226 provides a cam rotational axis oriented about perpendicular to longitudinal axis D-D.

As shown in FIGS. 15, 18, and 18B a cam slot 228 extends at least partially through the cam thickness 216 extending about parallel to left and right cam sides 220, 218. As illustrated in FIG. 18B, the slot 228 comprises a slot width 229 and a slot depth 231 that are dimensioned to receive the proximal end 206 of linkage 204. As shown, the cam slot width 229 spans along imaginary line E-E which is oriented about perpendicular to longitudinal axis D-D. The slot depth 231 extends along imaginary line F-F which is oriented about perpendicular to imaginary line E-E. In a preferred embodiment, the proximal linkage end 206 is positioned within the cam slot 228 and connected therewithin. A third pin (not shown) is positioned through cam openings 234A, 234B that respectively extend about perpendicular through right and left cam portions 210A, 210B thereby securing the linkage 204 to the cam 210. A fourth pin 236 is positioned through the linkage distal end opening 238 and through respective right and left U-Joint openings 240A and 240B at the drive shaft proximal end 200.

In addition, as illustrated in FIGS. 15, 18, 18A, and 18B, a third cam opening 242 having a length 243 extends at least partially through the thickness 216 of the cam 210. As shown, the opening 242 preferably positioned between respective left and right cam sides 218, 220 along imaginary line F-F. As illustrated in side view of FIG. 18A, the length 243 of opening 242 extends at least partially within the cam thickness 216 oriented at an angle with respect to imaginary lines G-G and H-H. As shown, imaginary line G-G extends about parallel to longitudinal axis D-D and imaginary line H-H extends about perpendicular to longitudinal axis D-D. In a preferred embodiment, the length 243 of opening 242 is oriented at about a 45° angle with respect to imaginary line G-G. Opening 242 is configured to receive the distal end 238 of the actuation lever 212. In a preferred embodiment, the third cam opening 242 may be threaded such that a correspondingly threaded distal actuation lever end 238 may be secured therewithin. A knob 244 may be connected to a proximal end 240 of the lever arm 212.

In a preferred embodiment, actuation of the lever arm 212 causes the drive shaft 198 to move in either a proximal or distal axial direction. More specifically, moving the lever arm proximal end 240 in a downward direction towards the base 160 of the platform 152 causes the cam 210 to rotate in a clockwise direction which thus causes the linkage 204 to move in a proximal direction away from the distal end 156 of the platform 152. The drive shaft 198 in turn also moves in a proximal direction toward the actuation lever 212. As a result, the drive shaft distal end 202 is retracted within the through bore 170 of the distal platform support 166. Likewise, actuation of the lever arm proximal end 240 in an upward direction away from the base 160 of the platform 152 causes the cam 210 to rotate in a counterclockwise direction which thus causes the linkage 204 to move in a distal direction toward the left platform support 166. This in turn moves the connected drive shaft 198 in a distal direction such that the drive shaft distal end 202 extends past the distal support sidewall surface 178 and within the interior 248 of the socket 172.

In a preferred embodiment, once the protective sleeve 10 or sleeve 10/ring 12 subassembly 66 is positioned within the socket interior 248, the actuation lever 212 is rotated in an angular direction with respect to the platform 150. In a preferred embodiment, the proximal end 240 of the actuation lever 212 is moved in an upward direction. This causes the drive shaft distal end 202 to distally extend so that it is positioned in contact with the proximal end surface 79 of the protective sleeve 10 or the sleeve 10/ring 12 subassembly 66. Thus, the drive shaft 198 ensures that the sleeve 10 or sleeve 10/ring 12 subassembly 66 is secured within the interior of the socket 172. Once the protective cover or sleeve 10/ring 12 subassembly 66 is secured within the socket interior 248, a force is applied in the proximal direction on the sleeve 10 or sleeve 10/ring 12 subassembly 66 to remove it from the end of the tool 18 or implant 20. In a preferred embodiment, the force is applied at the interface of the inner surface of the rim 250 and outer proximal surface of the sleeve 10 or sleeve 10/ring 12 subassembly 66. The tapered portion 24 of the implant 20 exits the distal socket opening 251 thus leaving the protective sleeve 10 or subassembly thereof 66 within the interior of the socket.

While the preferred embodiments of the surface protection system and methods have been described in reference to the environment in which they were developed, they are merely illustrative of the principles of the inventions. Other embodiments and configurations may be devised without departing from the spirit of the inventions and the scope of the appended claims.

Thus, it can be seen that the present invention provides a protection sleeve or sleeve/ring subassembly for covering a selected portion of an orthopedic implant. This is primarily for the purpose of providing one portion of the implant with a different surface finish than another portion. Specifically, the proximal tapered end of a femoral stem implant can be provided with a different surface finish than other portions of the implant. The present invention also describes a tool for removing the protective sleeve or sleeve/ring subassembly from the implant prior to use of the implant in an orthopedic procedure, such as a hip arthroplasty procedure.

What is claimed is:
1. A surface protection system, comprising:
 a) an orthopedic implant comprising an implant distal stem and a tapered implant proximal end, the tapered implant proximal end comprising an exterior surface;
 b) a sleeve comprising a sleeve proximal end and a tapered sleeve distal end, the tapered sleeve distal end comprising a distal edge and an interior surface, wherein the interior surface of the tapered sleeve distal end is matable with the exterior surface of the tapered implant proximal end;
 c) an impactor configured to form a sleeve-implant assembly, the impactor comprising: (i) an impactor rod having an impactor rod proximal end and an impactor rod distal end, the impactor rod being oriented along a first longitudinal axis, (ii) an impactor hammer, and (iii) an impactor coupling portion, each of the impactor hammer and the impactor coupling portion being oriented along the impactor rod such that the impactor coupling portion resides at the impactor rod distal end with the impactor hammer residing between the impactor rod proximal end and the impactor coupling portion, and wherein the impactor coupling portion has an annular sidewall that defines a coupling cavity configured to receive the sleeve, d) wherein with the sleeve received in the impactor coupling portion and with the sleeve positioned adjacent to the tapered implant proximal end, the impactor hammer is moveable along the impactor rod to contact and impart an impaction force to the impactor coupling portion that is sufficient to position the sleeve on the tapered implant proximal end, thereby forming the sleeve-implant assembly; and e) an extractor comprising a socket configured to receive the sleeve-implant assembly through an extractor socket side opening, wherein the socket has at least one socket interior rim configured to engage the distal edge of the tapered sleeve distal end after the sleeve-implant assembly has been formed, and wherein the extractor is configured to remove the sleeve from the tapered implant proximal end after the sleeve-implant assembly has been received in the socket through the extractor socket side opening with the distal edge of the tapered sleeve distal end engaged to the at least one socket interior rim.

2. The surface protection system of claim 1, wherein the impactor further comprises:

an impactor plate positioned at the impactor rod proximal end, the impactor plate oriented perpendicular to the first longitudinal axis such that the impactor plate provides a surface for a user to hold and apply the impaction force.

3. The surface protection system of claim 1, wherein the extractor further comprises:

a) a threaded member extending along a second longitudinal axis, the threaded member having a threaded member proximal end and a threaded member distal end;

b) an extractor handle; and c) an extractor plate orientated perpendicular to the second longitudinal axis, wherein the extractor plate has an extractor plate opening, d) wherein the threaded member is configured to rotatably couple the extractor handle to the extractor plate, and wherein the threaded member extends from the handle to the extractor plate opening, and further wherein with the sleeve-implant assembly received in the socket through the extractor socket side opening, rotation of the extractor handle: (i) positions the threaded member distal end in contact with the sleeve proximal end, and (ii) engages the distal edge of the tapered sleeve distal end with the at least one socket interior rim to form a secured extraction assembly such that when an extraction force sufficient to remove the sleeve from the tapered implant proximal end of the orthopedic implant is applied to the secured extraction assembly, the sleeve is removed from the orthopedic implant.

4. The surface protection system of claim 1 further comprising an annular ring, the annular ring being circumferentially positionable over the tapered sleeve distal end such that the annular ring structurally stabilizes the sleeve, thereby forming a stabilized sleeve, and directs the impaction force to the sleeve when the impaction force is applied to the stabilized sleeve.

5. The surface protection system of claim 1 further comprising an extractor mechanism, wherein the extractor mechanism comprises:

a) a platform residing on an imaginary base plane, the platform comprising: (i) a platform base having a platform base proximal end with a proximal support extending upwardly therefrom, and (ii) a platform base distal end with a distal support extending upwardly therefrom, wherein the proximal support and the distal support each reside along respective planes that are perpendicular to the imaginary base plane, b) wherein the distal support has a thickness with a throughbore oriented along a second longitudinal axis extending through the thickness of the distal support, and c) wherein the proximal support comprises parallel first and second proximal support walls that are separated by a gap and extend longitudinally along the platform base parallel to the second longitudinal axis, each of the first and second proximal support walls possessing a thickness, and wherein a first hole extends through the first proximal support wall thickness and a second hole extends through the second proximal support wall thickness, each of the first hole and the second hole being aligned along an imaginary axis that is perpendicular to the second longitudinal axis;

d) a drive shaft having proximal and distal drive shaft ends, wherein at least a portion of the distal drive shaft end is positionable in the throughbore, and wherein the proximal drive shaft end comprises a U-joint having spaced apart right and left sidewalls, each of the right sidewall and the left sidewall having respective right and left sidewall openings;

e) a cam residing in the gap between the first and second proximal support walls, the cam comprising a cam thickness extending between first and second cam face walls, each of the first cam face wall and the second cam face wall residing in respective planes parallel to the first and second proximal support walls, the cam further comprising a slot oriented along an imaginary slot plane perpendicular to the cam thickness, the slot separating first and second regions of the cam thickness and extending through a middle portion of the cam, wherein the cam has at least one cam hole oriented along an axis parallel to the cam thickness such that the at least one cam hole extends through at least a portion of the slot and the first and second regions of the cam thickness, and wherein the cam has at least one cam aperture oriented along an axis generally perpendicular to the at least one cam hole;

f) a linkage having proximal and distal linkage ends, each of the proximal linkage end and the distal linkage end possessing respective linkage end openings, wherein the distal linkage end is positioned between the right and left sidewalls of the U-joint such that the distal linkage end opening is aligned with the respective right and left sidewall openings of the U-joint, thereby forming a first alignment, wherein a first pin extends through the first alignment to rotatably connect and secure the proximal drive shaft end to the distal linkage end, and wherein the proximal linkage end is positioned within the slot of the cam such that the proximal linkage end opening is aligned with the at least one cam hole to form a second alignment, wherein a second pin extends through the second alignment to rotatably connect and secure the cam to the proximal linkage end; and g) a lever having proximal and distal lever ends, wherein the distal lever end is positionable within the at least one cam aperture such that manipulation of the proximal lever end in a first direction rotates the cam thereby impelling the drive shaft along the second longitudinal axis such that with the sleeve-implant assembly received in the socket through the extractor socket side opening the drive shaft distal end extends to the sleeve proximal end, thereby securing the distal edge of the tapered sleeve distal end with the at least one socket interior rim to form a secured extraction assembly, wherein manipulation of the proximal lever end in a second direction, opposite to the first direction, retracts the drive shaft within the throughbore to impart an extraction force to the secured extraction assembly sufficient to remove the sleeve from the orthopedic implant.

6. A surface protection system, comprising:
a) an orthopedic implant comprising an implant distal stem and a tapered implant proximal end, the tapered implant proximal end comprising an exterior surface;
b) a sleeve comprising a sleeve proximal end and a tapered sleeve distal end, the tapered sleeve distal end comprising a distal edge and an interior surface, wherein the sleeve is positionable over at least a portion of the orthopedic implant such that the interior surface of the tapered sleeve distal end is matable with the exterior surface of the tapered implant proximal end to form a sleeve-implant assembly when the interior surface of the tapered sleeve distal end is mated with the exterior surface of the tapered implant proximal end; and
c) an extractor comprising a socket configured to receive the sleeve-implant assembly through an extractor socket side opening, wherein the socket has at least one socket interior rim configured to engage the distal edge of the tapered sleeve distal end after the sleeve-implant assembly has been formed, and wherein the extractor is configured to remove the sleeve from the orthopedic implant after the sleeve-implant assembly has been received in the socket through the extractor socket side opening with the distal edge of the tapered sleeve distal end engaged to the at least one socket interior rim.

7. The surface protection system of claim 6, further comprising:
d) an impactor configured to form the sleeve-implant assembly, the impactor comprising: (i) an impactor rod having an impactor rod proximal end and an impactor rod distal end, the impactor rod being oriented along a longitudinal axis, (ii) an impactor hammer, and (iii) an impactor coupling portion, each of the impactor hammer and the impactor coupling portion being oriented along the impactor rod such that the impactor coupling portion resides at the impactor rod distal end with the impactor hammer residing between the impactor rod proximal end and the impactor coupling portion, and wherein the impactor coupling portion has an annular sidewall that defines a coupling cavity configured to receive the sleeve, and
e) wherein with the sleeve received in the impactor coupling portion and with the sleeve positioned adjacent to the implant proximal end, the impactor hammer is moveable along the impactor rod to contact and impart an impaction force to the impactor coupling portion that is sufficient to position the sleeve on the tapered implant proximal end, thereby forming the sleeve-implant assembly.

8. A surface protection system, comprising:
a) a sleeve comprising a sleeve proximal end and a tapered sleeve distal end, the tapered sleeve distal end comprising a distal edge, wherein the sleeve is positionable over at least a portion of an orthopedic implant to form a sleeve-implant assembly; and
c) an extractor comprising:
   (i) a socket configured to receive the sleeve-implant assembly through an extractor socket side opening, wherein the socket has at least one socket interior rim configured to engage the distal edge of the tapered sleeve distal end after the sleeve-implant assembly has been formed, and wherein the extractor is configured to remove the sleeve from the portion of the orthopedic implant after the sleeve-implant assembly has been received in the socket through the extractor socket side opening with the distal edge of the tapered sleeve distal end engaged to the at least one socket interior rim;
   (ii) an extractor handle oriented perpendicular to a longitudinal axis;
   (iii) an extractor plate orientated perpendicular to the longitudinal axis, wherein the extractor plate has a thickness and an opening that extends through the extractor plate thickness; and
   (iv) a threaded member configured to adjustably couple the extractor handle to the extractor plate, the threaded member having a threaded member proximal end and a threaded member distal end, wherein the threaded member extends along the longitudinal axis from the extractor handle to the opening, and
   (v) wherein with the sleeve-implant assembly received in the socket through the extractor socket side opening, rotation of the extractor handle: (I) positions the threaded member distal end in contact with the sleeve proximal end, and (II) engages the distal edge of the tapered sleeve distal end with the at least one socket interior rim to form a secured extraction assembly such that when an extraction force sufficient to remove the sleeve from the portion of the orthopedic implant is applied to the secured extraction assembly, the sleeve is removed from the portion of the orthopedic implant.

* * * * *